(12) United States Patent
Mann et al.

(10) Patent No.: US 12,241,118 B2
(45) Date of Patent: Mar. 4, 2025

(54) ASSAY FOR THE RAPID DETECTION OF NUCLEIC ACIDS VIA A MODIFIED LAMP REACTION COUPLED WITH COLORIMETRIC REPORTER UTILIZING A GOLD NANOPARTICLE : PEPTIDE NUCLEIC ACID (AuNp-PNA) PROBE SYSTEM

(71) Applicants: Paul Mann, Marquette, MI (US); Matthew Jennings, Marquette, MI (US)

(72) Inventors: Paul Mann, Marquette, MI (US); Matthew Jennings, Marquette, MI (US)

(*) Notice: Subject to any disclaimer, the term of this patent is extended or adjusted under 35 U.S.C. 154(b) by 0 days.

(21) Appl. No.: 17/821,277

(22) Filed: Aug. 22, 2022

(65) Prior Publication Data
US 2023/0227898 A1    Jul. 20, 2023

Related U.S. Application Data

(63) Continuation of application No. 16/706,243, filed on Dec. 6, 2019, now abandoned.

(60) Provisional application No. 62/776,104, filed on Dec. 6, 2018.

(51) Int. Cl.
*C12Q 1/68* (2018.01)
*C12Q 1/6806* (2018.01)
*C12Q 1/6816* (2018.01)
*C12Q 1/6853* (2018.01)
*C12Q 1/6869* (2018.01)

(52) U.S. Cl.
CPC ......... *C12Q 1/6853* (2013.01); *C12Q 1/6806* (2013.01); *C12Q 1/6816* (2013.01); *C12Q 1/6869* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

PUBLICATIONS

Jaroenram, W., et al. Rapid and sensitive detection of shrimp yellow head virus using loop-mediated isothermal amplification and a coloregenic nanogold hybridization probe. J. Virol. Methods, vol. 186, p. 36-42, (2012).*

Itonaga. M., et al. Novel methodology for rapid detection of KRAS mutation using PNA-LNA mediated loop-mediated isothermal amplification. PLOS one, vol. 11(3): e0151654, p. 1-12, (2016).*

* cited by examiner

*Primary Examiner* — Suryaprabha Chunduru
(74) *Attorney, Agent, or Firm* — Mark L. Maki; Miller Canfield

(57) ABSTRACT

An assay is provided for the rapid detection of nucleic acids via a modified LAMP reaction coupled with colorimetric reporter utilizing a gold nanoparticle—peptide nucleic acid (AuNP-PNA) probe system.

10 Claims, 9 Drawing Sheets

Modification of LAMP primer for detection of HIV

Overall scheme for detection of nucleic acids

Proof of principle for the genera on of a specific PNA target sequence

HIV p24 Colorimetric Detection  Staph. aureus Colorimetric Detection
Poly T (-) PNA(+)              Poly T(-) PNA (+)

AuNP / PNA Probe Colorimetric Detection

FIG. 6A
FIG. 6B
FIG. 6C
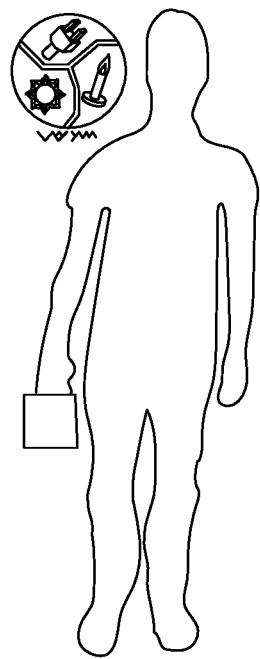
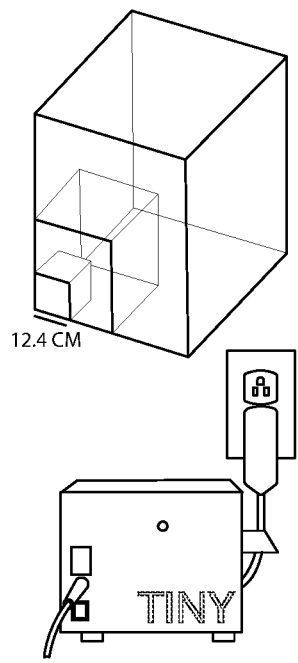
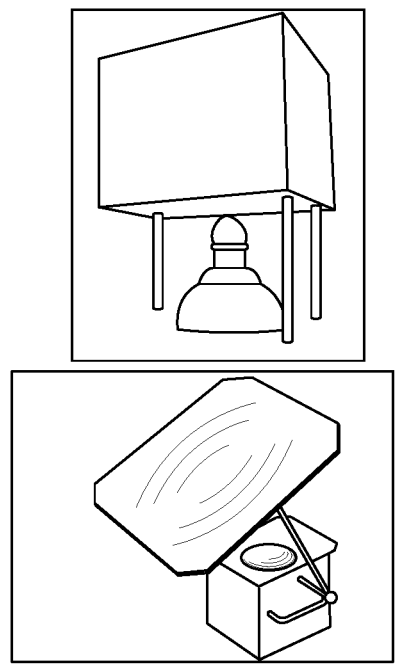
FIG. 6D
FIG. 6E

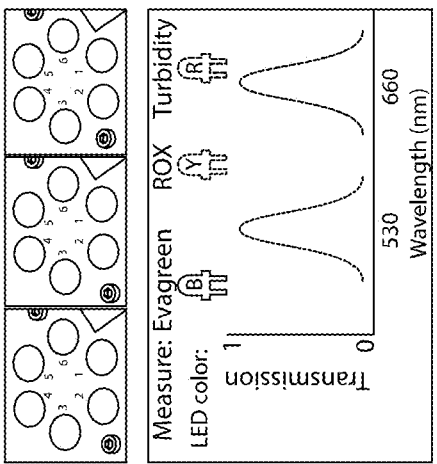
FIG. 7A
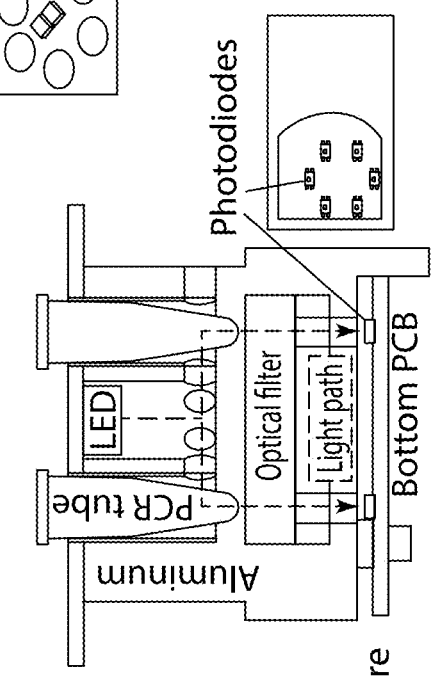
FIG. 7B
FIG. 7C
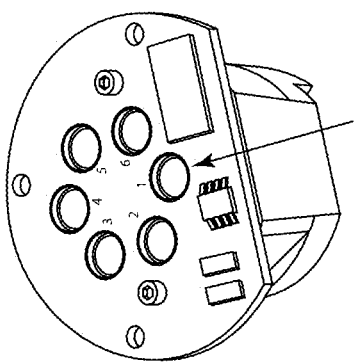
FIG. 7D
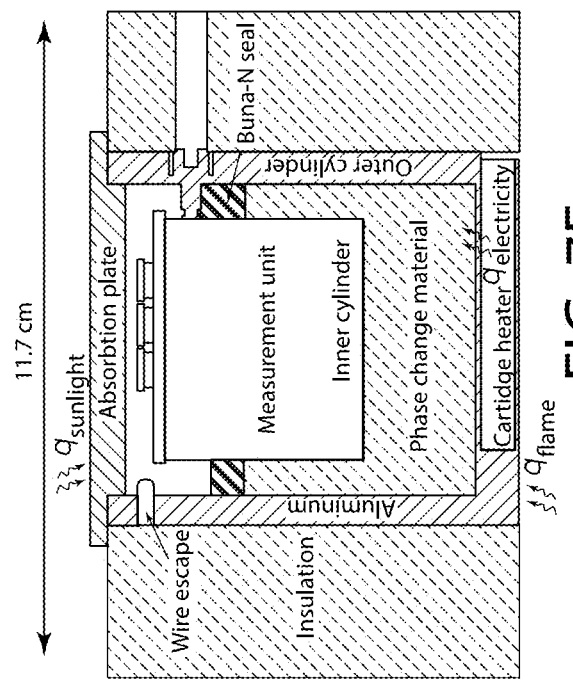
FIG. 7E

ASSAY FOR THE RAPID DETECTION OF NUCLEIC ACIDS VIA A MODIFIED LAMP REACTION COUPLED WITH COLORIMETRIC REPORTER UTILIZING A GOLD NANOPARTICLE : PEPTIDE NUCLEIC ACID (AuNp-PNA) PROBE SYSTEM

CROSS REFERENCE TO RELATED APPLICATIONS

This application is a continuation application of U.S. patent application Ser. No. 16/706,243, filed Dec. 6, 2019, which in turn claims priority of U.S. Provisional Patent Application No. 62/776,104, filed Dec. 6, 2018, the disclosures of which applications are hereby incorporated by reference in their entireties.

FIELD OF THE INVENTION

The invention relates to an assay for the rapid detection of nucleic acids via a modified LAMP reaction coupled with colorimetric reporter utilizing a gold nanoparticle—peptide nucleic acid (AuNP-PNA) probe system.

BACKGROUND OF THE INVENTION

An isothermal molecular technique known as Loop Mediated Isothermal Amplification (LAMP) allows for amplification and detection of specific nucleic acid sequences. LAMP is a culture-independent nucleic acid amplification technique that is more specific and sensitive than traditional polymerase chain reaction (PCR). LAMP assays have been adapted for rapid detection (less than 30 minutes) of nucleic acids and can be performed without nucleic acid extraction steps, making this technology highly amenable for point-of-care assays. Colorimetric LAMP assays allow the user to detect a potentially positive result as a result of a color change in the reaction vessel. Several colorimetric reporter systems have been used to include pH sensitive or organic dyes. While convenient, these reporter systems do not detect the presence of a specific nucleic acid sequence and thus have the potential for false positives.

It is an object of the invention to provide an improved rapid diagnostic assay for detection of nucleic acids.

SUMMARY OF THE INVENTION

The invention relates to an improved rapid diagnostic assay for detection of nucleic acids (DNA/RNA). The inventive process utilizes isothermal nucleic acid amplification technology coupled with a gold nanoparticle (AuNP)/peptide nucleic acid (PNA) colorimetric probe system. For descriptive purposes, the assay can be divided into two components; 1) isothermal amplification of a target dependent sequence and 2) AuNP/PNA probe colorimetric detection of the isothermal amplified sequence. The inventive assay combines a modified LAMP technology with a AuNP/PNA probe based detection method to create a sequence specific colorimetric LAMP assay. The advantage of this approach is the superior specificity of the AuNP/PNA probe system compared to conventional colorimetric LAMP methods. It is believed that this is the first sequence specific colorimetric LAMP assay system developed.

Other objects and purposes of the invention, and variations thereof, will be apparent upon reading the following specification and inspecting the accompanying drawings.

BRIEF DESCRIPTION OF THE DRAWINGS

FIG. 6A shows the TINY LAMP device relative to another object, namely a human.

FIG. 6B shows the TINY LAMP device relative to other larger objects such as GeneXpert IV by Cepheid or a ViiA 7 Real-Time PCR System.

FIG. 6C shows the TINY LAMP device relative to a Bunsen burner.

FIG. 6D shows the TINY LAMP device in use with an alternate power source, namely being heated via electricity.

FIG. 6E shows the TINY LAMP device in use with an alternate power source, namely being heated via sunlight.

FIG. 7A illustrates components of the LAMP device comprising a measurement unit separated from a temperature regulation unit.

FIG. 7B illustrates the temperature-regulation unit.

FIG. 7C illustrates that when an LED color wherein blue, yellow and red indicate measurement of Evagreen dye, ROX dye, and turbidity.

FIG. 7D illustrates a measurement unit in the center of the temperature-regulation unit.

FIG. 7E illustrates a cross section of the temperature-regulation unit.

FIGS. 11A and 11B 8 are graphs showing performance results.

Figure 1:
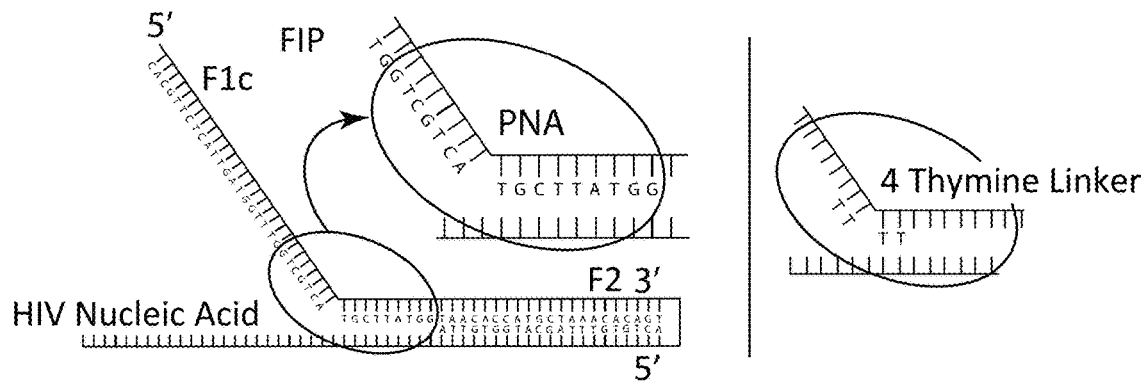
FIG. 1 diagrammatically shows the modification of LAMP primer for detection of nucleic acids and identification of a specific target sequence such as that association with Human Immunodeficiency Virus (HIV).

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. Said terminology will include the words specifically mentioned, derivatives thereof, and words of similar import.

DETAILED DESCRIPTION

As described herein with reference to FIGS. 1-4, the invention successfully performs the assay described below on both a viral pathogen (HIV) and a bacterial pathogen (*Staphylococcus aureus*).

The invention exhibits several aspects of novelty as follows:
1) Improved specificity over a traditional LAMP assay.
2) Modification of LAMP primers for the generation of a target dependent sequence (FIG. 1).
3) Colorimetric detection of the target dependent sequence via a AuNP/PNA (gold nanoparticle/peptide nucleic acid) probe system (FIGS. 2 and 4).
4) It is believed that this is the first colorimetric assay to be specific for detection of a LAMP product. Previous colorimetric methodologies are indirect measures of LAMP amplification.

The invention relates to an assay and method developed as a rapid diagnostic assay for detection of nucleic acids (DNA/RNA). The process utilizes isothermal nucleic acid amplification technology coupled with a gold nanoparticle (AuNP)/peptide nucleic acid (PNA) colorimetric probe system. For descriptive purposes, the assay can be divided into two components; 1) isothermal amplification of a target dependent sequence and 2) AuNP/PNA probe colorimetric detection of the isothermal amplified sequence. A robust, isothermal molecular technique known as Loop Mediated Isothermal Amplification (LAMP) allows for amplification and detection of specific nucleic acid sequences. LAMP is a culture-independent nucleic acid amplification technique that is more specific and sensitive than traditional polymerase chain reaction (PCR). LAMP assays have been adapted for rapid detection (less than 30 minutes) of nucleic acids and can be performed without nucleic acid extraction steps, making this technology highly amenable for point-of-care assays. Colorimetric LAMP assays allow the user to detect a potentially positive result as a result of a color change in the reaction vessel. Several colorimetric reporter systems have been used to include pH sensitive or organic dyes. While convenient, these reporter systems do not detect the presence of a specific nucleic acid sequence and thus have the potential for false positives. The inventive assay combines a modified LAMP technology with a AuNP/PNA probe based detection method to create a sequence specific colorimetric LAMP assay. The advantage of this approach is the superior specificity of the AuNP/PNA probe system compared to conventional colorimetric LAMP methods. It is believed that this is the first sequence specific colorimetric LAMP assay system developed.

Figure 4:
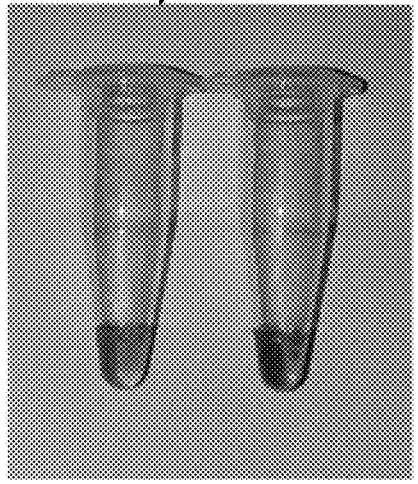
FIG. 4 shows the AuNP/PNA probe colorimetric detection in test samples.
Figure 4:
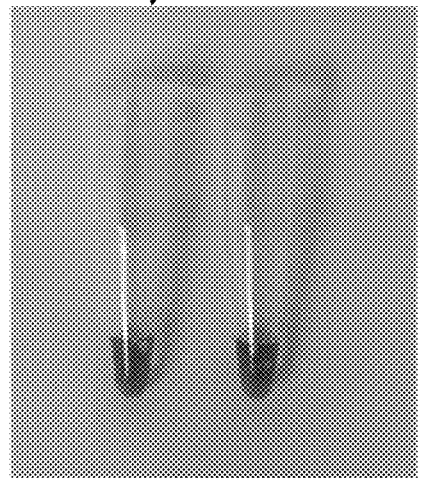

The novelty of this assay is that the modified LAMP reactions of the invention will simultaneously generate a target specific sequence that serves as the site for a PNA probe during the colorimetric detection. The LAMP reaction utilizes a minimum of four primers (FIP, BIP, F3, B3) that recognize six target sequences. The inventive assay makes a modification to the FIP and BIP primers where the traditional poly T linker is replaced with a PNA sequence (FIG. 1). In this method, LAMP mediated amplification of nucleic acid will generate a specific DNA sequence that is the complement of, and target for, the PNA probe. The presence of the PNA/DNA hybrid will then be detected using a colorimetric reporter system. The aggregative properties of gold nanoparticles (AuNPs) allow them to be used to detect PNA/DNA hybrids. Non-aggregated AuNPs appear red in solution while aggregated AuNPs appear blue. Interactions between PNAs and AuNPs cause them to aggregate. In the presence of a binding partner (target dependent LAMP generated DNA sequence) and the subsequent formation of the PNA/DNA hybrid, the gold nanoparticles remain monodisperse and are red in solution. Thus, in the case of a positive LAMP reaction, the PNA binds to the LAMP generated target sequence and the solution remains red. However, in the absence of the target DNA sequence (i.e. negative LAMP reaction); the unbound PNA promotes AuNP aggregation resulting in a visually detectable blue color (FIGS. 2 and 4).

FIG. 1 shows the modification of LAMP primer for detection of HIV. Shown in the circles are the linker sequence found in FIP (Forward Inner Primer). On the right is the traditional linker sequence in FIP. The left demonstrates the modification used for the generation of target dependent sequence. In the inventive assays, both FIP and BIP primers contain the PNA sequence.

Figure 2:
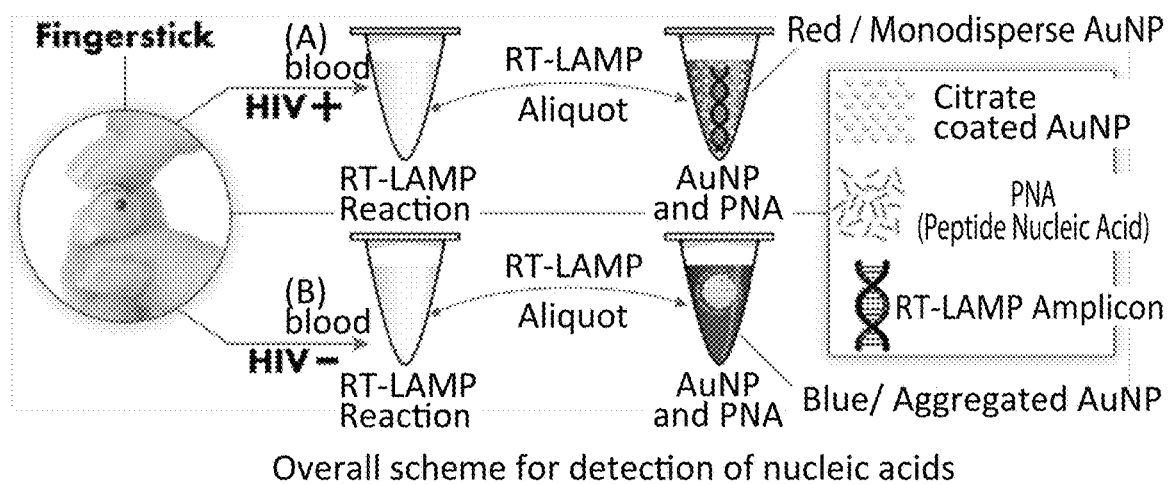
FIG. 2 diagrammatically shows an overall scheme for detection of nucleic acids.

FIG. 2 shows an overall scheme for detection of nucleic acids. In the example shown, the LAMP assay detects HIV (because HIV nucleic acid is RNA, the LAMP reaction is a Reverse Transcriptase-LAMP reaction). In an HIV positive sample, the PNA recognizes the LAMP amplified target dependent sequence and hybridizes to that sequence. The AuNP remain monodisperse and red in solution in an HIV positive sample. In an HIV negative sample, there is no amplification product generated. Therefore, the PNA probe has no target and causes the AuNP to aggregate resulting in a blue solution.

Figure 3:
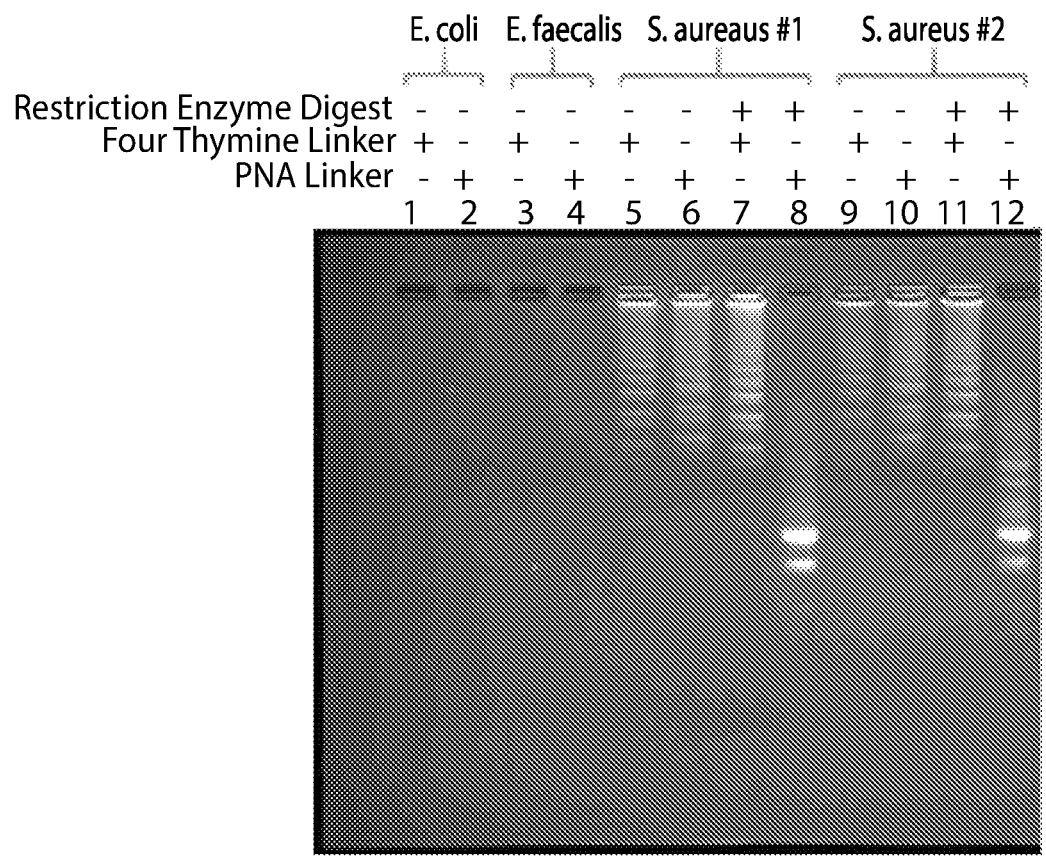
FIG. 3 comprises test results showing proof of principle for the generation of a specific PNA target sequence.

FIG. 3 shows proof of principle for the generation of a specific PNA target sequence with LAMP amplification of the *Staphylococcus aureus* nuclease gene in the presence of the four thymine linker (lanes 5,7,9,11) and the 16 base complementary sequence to PNA (lanes 6,8,10,12). The presence of a typical laddering pattern in lanes 5-7 and 9-11 indicate a positive LAMP reaction. Lanes 1-4 were negative controls. LAMP amplicons in lanes 7, 8, 11, and 12 were treated with the restriction enzyme, Ms1I, that recognizes a target sequence within the PNA. Confirmation of the presence of the complementary PNA sequence is shown by digestion of the LAMP products as seen in lanes 8 and 12.

To demonstrate the incorporation of the target dependent sequence in the inventive LAMP product, a restriction enzyme is utilized to cut LAMP amplicons containing the PNA sequence (FIG. 3). In the presence of *Staphylococcus aureus*, there is target specific amplification in primer sets containing the four thymine linker as well as the PNA sequence. However, the restriction enzyme only recognizes a sequence found within the PNA linker. Comparing the migration pattern of LAMP products of lanes 7 versus 8 and 11 versus 12 demonstrates the generation of the target dependent sequence.

For AuNP/PNA probe colorimetric detection of LAMP amplicon, the PNA serves two functions: 1) sequence specific probe hybridization of the target and 2) unbound PNA promotes aggregation of the AuNP. Gold nanoparticles are evaluated with visual color indication by monodispersion (red) and aggregation (blue) states. The AuNP colorimetric detection of PNA:DNA complexes occurs. The sequence specific colorimetric detection of LAMP amplicon with PNA probes was achieved with a two-step hybridization and detection procedure. A 10 µL preincubation mixture containing 0.3 µM of PNA, 0.2× Phosphate Buffer Saline (2 mM phosphate, 27.4 mM NaCl, and 0.54 mM KCl, at pH 7.4) and 1 µL of LAMP DNA amplicon was heated at 95° C. for 5 minutes for complete DNA denaturation. The DNA-PNA preincubation mixture was snap-cooled on ice for 2 minutes to preserve the single stranded DNA. The mixture was allowed to reach room temperature over a 5-minute period to allow PNA probe hybridization. Lastly, 10 µL of AuNP were added, for a final volume of 20 µL that contained 1 nM of AuNP. The colorimetric results were visualized after 1 minute (FIG. 4).

FIG. 4 shows the AuNP/PNA probe colorimetric detection. Using both an HIV target (p24) and a *Staphylococcus aureus* target (nuclease gene), the AuNP/PNA probe colorimetric detection system was able to distinguish between target specific amplification of the poly T sequence (negative, blue) and the target specific amplification of the PNA sequence (positive, red). In a colorized version of FIG. 4, Poly T (−) would show in blue and PNA(+) would show in red for both the HIV p24 Colorimetric Detection and the *Staph. aureus* Colorimetric Detection.

In accord with the above-description of FIGS. 1-4, the invention successfully performs the assay on both a viral pathogen (HIV) and a bacterial pathogen (*Staphylococcus aureus*).

In further detail, the inventive assay is suitable for the rapid detection of HIV using an energy flexible portable system and novel reporter system.

In more detail, rapid identification of Human Immunodeficiency Virus (HIV) infection status is imperative for limiting spread of the virus. Currently, there are no rapid point-of-care testing methods capable of detecting HIV prior to the onset of an immune response. To address this shortcoming, a rapid nucleic acid-based diagnostic assay amenable has been developed for use in a point-of-care device. The process utilizes isothermal nucleic acid amplification technology coupled with a gold nanoparticle (AuNP)/peptide nucleic acid (PNA) probe based colorimetric detection system. The invention can optimize the assay for use in a device named, TINY (Tiny Isothermal Nucleic acid quantification sYstem). The TINY platform allows for portable and energy-flexible nucleic acid-based identification using an isothermal amplification method and colorimetric readout. The assay and device are developed for use as a point-of care test capable of performing in an austere environment.

Figure 5:
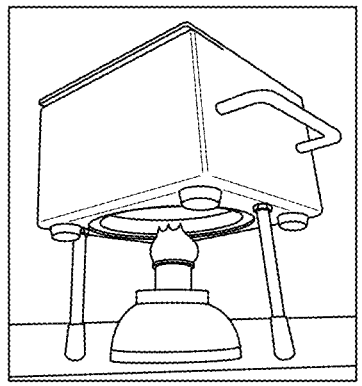
FIG. 5 is a pictorial view showing a LAMP device.

The inventive assay performs RT-LAMP (Reverse Transcriptase—Loop Medicated Isothermal Amplification) of HIV viral RNA from whole blood. The detection of the RT-LAMP amplicon is based on interactions between AuNP and amplicon specific PNA. These interactions determine the aggregative state of the AuNP which results in a color change of the reaction where an HIV positive sample is red and an HIV negative sample is blue (FIG. 2). The RT-LAMP reaction and colorimetric detection are performed, for example, in the TINY platform (FIG. 5). FIG. 5 shows a TINY device of Cornell University, which is a 6-plex portable nucleic acid quantification system for austere settings.

Referring to FIG. 2 discussed above, this figure provides an overview of proposed rapid, molecular point-of-care HIV assay. Finger stick blood from an individual is placed into the RT-LAMP reaction tube. After the RT-LAMP reaction, an aliquot is removed from the RT-LAMP tube and added to a second tube containing AuNPs and PNA. Sequence A results in a finding of HIV Positive, wherein upon addition of the aliquot, the PNA will hybridize with the RT-LAMP generated HIV dependent amplicon allowing the AuNPs to remain monodispersed resulting in a red solution. Sequence B results in a finding of HIV Negative wherein in the absence of the HIV dependent sequence, the PNA is free to induce AuNP aggregation resulting in a blue solution.

To deploy the technology in both clinical and limited resource settings, the invention adapts the TINY (Tiny Isothermal Nucleic acid quantification sYstem) technology, which is a platform for portable and energy-flexible nucleic acid-based identification using a LAMP isothermal amplification method and fluorescence readout. The current system, shown in FIG. 5 is able to perform 6 independent reactions in parallel—making it ideally suited for this application. The energy required to operate TINY may be supplied via electricity, but may also be supplied via sunlight or flame for operation in locations without electricity. As part of an effort to develop point-of-care cancer diagnostic technologies for austere settings, TINY has been evaluated for the identification and quantification of Kaposi's sarcoma-associated herpesvirus (KSHV) DNA in human biopsies.

The present invention can be optimized through a research plan having several phases with the following specific aims:

R61 Phase:

Specific Aim #1: Optimize a rapid and novel isothermal nucleic acid amplification technique that generates a target amplicon that is detected by a AuNP/PNA probe based colorimetric detection system.

Specific Aim #2: Optimize a simple visual colorimetric reporter system utilizing AuNP/PNA probe colorimetric detection system that detects the PNA/DNA hybrid from HIV positive RT-LAMP reaction samples.

Specific Aim #3: Evaluate and optimize the performance characteristics of the novel assay on clinical samples with known HIV status and viral load levels ranging between 200 and 100,000 copies/ml.

Specific Aim #4: Adapt the TINY system for colorimetric quantification consistent with the AuNP/PNA probe reporter system.

R33 Phase:

Specific Aim #5: Clinical validation of the TINY system for HIV detection.

Specific Aim #6: Validation of the TINY system for HIV detection in an austere environment.

As further background for this invention, the World Health Organization (WHO) developed recommendations to control the spread of the HIV virus. Central to this policy is the rapid determination of HIV infection status and immediate initiation of anti-retroviral therapy upon a positive result to prevent the predicted 1.8 million new yearly infections (WHO HIV/AIDS fact sheet). While 70% of HIV-positive people are aware of their HIV status, to reach WHO's target of 90%, an additional 7.5 million people need access to HIV testing. Implementation of the proposed assay would have a significant impact on the ability of large populations of individuals to test themselves easily and accurately. Because the inventive assay would not require medical infrastructure (refrigeration, laboratory equipment, or training) or a nucleic acid extraction step, it is believed that reaching or exceeding the WHO goal of 90% is feasible.

Conventional laboratory methods for HIV detection use immunoassays that detect HIV antibodies or p24 antigen. The U.S. Centers for Disease Control and Prevention (CDC) and the Association of Public Health Laboratories published an updated HIV testing algorithm in 2018. This guidance recommends an antigen/antibody combination immunoassay that detects HIV-1 and HIV-2 antibodies and the HIV-1 p24 antigen as the confirmatory testing method. While improved from previous generation testing assays, these immunologically based methods lack the required sensitivity as they depend on an antibody response not detectable until weeks after HIV exposure or high levels of circulating p24 antigen. While laboratory based RNA HIV assays are available, the instability of the nucleic acid prohibits the use of these tests as screening methods, especially in remote locations.

There is also an FDA approved over-the-counter test where the individual submits a sample via mail for antibody testing. Results are then available in one to two days via telephone. Additionally, an antibody based home test is available that uses oral fluid for the sample. The test result is available in as little as 20 minutes; however, this assay has reduced sensitivity due to lower antibody levels in saliva. Neither of these tests provide HIV infection status information timely enough to achieve the WHO goals. As rapid immunoassays are dependent on the development of an infected individual's immune response, and that response cannot be enhanced by technology, a neoteric approach is necessary. This underscores the importance of using point-of-care nucleic acid based tests to detect HIV infection.

Current point-of-care or self-testing assays do not provide HIV status to individuals such that informed decisions regarding lifestyle and treatment can be made expeditiously because HIV status may not be detected early in an infection. The scientific community is tasked with developing a means for rapid determination of HIV status, ideally by detecting HIV nucleic acid prior to the formation of a detectable antibody response, for use in a point-of-care or self-testing environment.

To meet this goal, the inventors have developed a novel nucleic acid-based diagnostic HIV test that uses isothermal nucleic acid amplification to generate a unique HIV-dependent target sequence coupled with an AuNP/PNA probe colorimetric detection system. This technique circumvents the limitations of antibody-based testing, as the viral nucleic acid is the ideal indicator of HIV infection and can be detected within days of exposure. Because this assay will not require a nucleic acid extraction step and is performed with a single heat source, access to advanced equipment and/or electricity is not essential. This assay may be performed on whole blood with lyophilized reagents utilizing the TINY system. The characteristics of isothermal amplification and AuNP/PNA probe make this proposed assay compatible detection using appropriate equipment such as the TINY system with the long-term goal of a rapid, robust HIV test performed by individuals within the privacy of their own home.

Referring to FIG. 6, the TINY system is one hardware option arising from a desire to create a field portable, point-of-care, rugged, diagnostic tool for quantifying the nucleic acid content of suspected KS biopsies in settings where little to no reliable infrastructure may be present. TINY enables nucleic acid quantification in a handheld package (FIG. 6A), and its weight and volume an order of magnitude smaller when compared to commercial quantitative PCR (qPCR) machines (FIG. 6B). Key to its versatility is that TINY can use a variety of energy sources (thermal, electricity, solar—FIG. 6C, 6D, 6E) to operate because it stores heat isothermally through use of a phase change material (PCM). The latent heat of the melted PCM inside TINY also allows the system to continue operating in case of power outages or variable cloud coverage. 0.2 mL PCR tubes are used as plastic consumables, as they are inexpensive and easily accessible, and facilitate the 6× multiplexing. The invention intends to target four HIV targets and use the remaining two reactions for internal positive and negative controls.

Referring further to FIG. 6, FIG. 6A shows that TINY is portable and easily carried in one hand, and FIG. 6B shows that TINY is much smaller than the GeneXpert IV by Cepheid, or the ViiA 7 Real-Time PCR System. FIG. 6C shows that TINY can be heated by a Bunsen burner, while FIG. 6D shows TINY heated via electricity and FIG. 6E shows TINY heated via concentrated sunlight, as such is done at the Infectious Diseases Institute in Uganda.

Referring to FIG. 7, TINY comprises a temperature-regulation unit and measurement unit. The temperature-regulation unit is responsible for heat collection and isothermal stabilization. The measurement unit is responsible for tracking the progress of the nucleic acid amplification (FIGS. 7A and 7B). LEDs affixed to the top excite commonly used fluorophores in the sample (FIG. 7C). A dual bandpass optical filter is placed above photodiodes on the bottom PCB, allowing TINY to measure both fluorescence and absorbance by cycling the active LED.

In more detail as to FIG. 7, FIGS. 7A and 7B shows the construction and design of TINY. FIG. 7C shows the measurement unit separated from the temperature-regulation unit and shows the LEDs are placed on the bottom side of the top PCB. When the LED: shines blue, Evagreen dye is measured; shines yellow, ROX dye is measured; and shines red, turbidity is measured. FIG. 7D shows the measurement unit in the center of the temperature-regulation unit. FIG. 7E shows a cross section of the temperature-regulation unit.

More particularly as to the research phases, in the R61 Phase, specific aims are pursued as follows.

R61 Phase, Specific Aim #1: Optimize a rapid and novel isothermal nucleic acid amplification technique that generates a target amplicon that is detected by a AuNP/PNA probe based colorimetric detection system.

This phase will establish a simple, rapid, and portable nucleic acid-based test for HIV using isothermal amplification and colorimetric detection. The assay will be capable of detecting HIV early in infection prior to the generation of a detectable immune response, in contrast to the antibody-based methodology currently employed that target markers generated weeks after infection. The proposed assay is amenable to public consumption, as it will not require nucleic acid extraction, access to electricity or complicated equipment, nor scientific expertise. Reagents will be lyophilized and the assay will only require a heat source and device to measure absorbance. All the consumer would need to provide is a small volume (droplet) of blood and within 45 minutes, the individual is then informed of their HIV infection status. The ability of the consumer to determine their HIV status using a nucleic acid based method rather than by antibody detection will significantly reduce the amount of time post exposure in which the infection is unknown. This enhanced identification will facilitate improved lifestyle choices, access to earlier treatment, and reduce spread of the HIV virus.

LAMP is a relatively new nucleic acid amplification technique that rapidly and specifically detects target DNA sequences. Three hallmarks of this method include isothermal conditions, high specificity and high amplification efficiency. LAMP utilizes the Bst DNA polymerase, which has strand displacement activity and lacks 5'-3' exonuclease activity. This property eliminates the need for a thermal cycler, and the method can be performed with any piece of equipment that maintains a constant temperature, such as a water bath, heat block or chemical heat pack, and therefore does not require expensive laboratory equipment. Traditionally, LAMP amplification is detected by fluorescence, turbidity, or pH changes. Recently colorimetric detection methods have been developed. However, none of these colorimetric detection methods is sequence specific, but rather depend on indirect detection of amplification by-products and therefore may be prone to false positives.

A pH based colorimetric method is the best-characterized colorimetric detection method. When Bst polymerase incorporates a dNTP during synthesis pyrophosphate and hydrogen ions are released. Phenol red, a pH indicator dye, can be incorporated into the reaction tube to visualize the drop in pH. This provides the added benefit of not requiring extensive personnel training or data analysis. While the read-out for the proposed assay does not use pH as an indicator, this method can easily be used to evaluate the assay.

A second hallmark of LAMP involves its high specificity compared to conventional amplification methods, such as PCR. This is due to the use of four primers designed to recognize six distinct sequences on the target. The process is extremely efficient and creates approximately $10^9$ amplicons of various sizes in less than an hour. These amplicons generate a laddering pattern upon agarose gel electrophoresis rather than the single band associated with conventional amplification techniques. LAMP can be performed on cell lysates eliminating the requirement for a nucleic acid extraction step. LAMP can be coupled with a reverse transcriptase step to detect RNA sequences (RT-LAMP) as shown recently to detect acute HIV infection suggesting it is a viable technique for initial early detection of HIV infection status. LAMP has been successfully performed using heat blocks, water baths, and electricity free heat sources. More recently, a smartphone-based application has been coupled with electricity free incubation to detect a LAMP reaction. These characteristics make LAMP based assays well suited for point of sample collection, non-laboratory, testing environments.

Figure 8A:
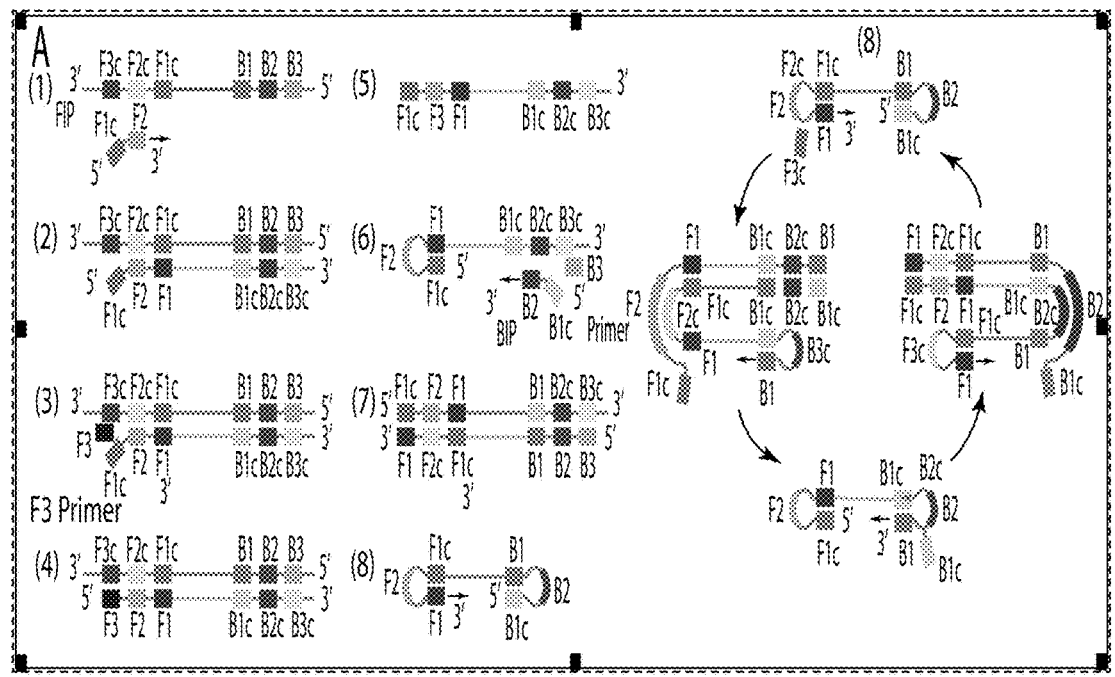
FIG. 8A is schematic of the LAMP reaction.

The high specificity of LAMP compared to other amplification methods is due to the use of four primers designed to recognize six distinct sequences on the target. The F3 and B3 primers are the outer primers that flank the region of interest (FIG. 8A). The FIP (F2 and F1c) and BIP (B2 and B1c) stand for forward inner primer and backward inner primer, respectively, and are unique in that they each recognize two different regions on the target DNA. Conventionally, the two different primer regions are linked by four thymines (TTTT) that provides flexibility to the newly generated sequence and allows for the creation of a unique dumbbell shaped initial LAMP template. After initial strand displacement by Bst DNA polymerase, the F2 region of the FIP binds to its complementary sequence and is extended. The F3 primer then binds upstream from the FIP and displaces the newly synthesized strand resulting in two products: a double stranded DNA and single stranded DNA. The single stranded DNA is used as a template for the reverse reaction primed by the BIP and B3 primers. The resulting product is a single stranded dumbbell structure that is the true starting template for the LAMP process. The FIP and BIP serve a dual purpose: they create the starting template and prime the rest of the amplification process by annealing to complementary sequences on the newly synthesized loops. An additional two primers, called loop primers, can also be incorporated into the LAMP process, which can cut the reaction time by as much as half compared to the original method. Loop primers are designed to be complementary to the regions between F1c and F2 or B1c and B2 on the single stranded dumbbell structures.

Figure 8B:
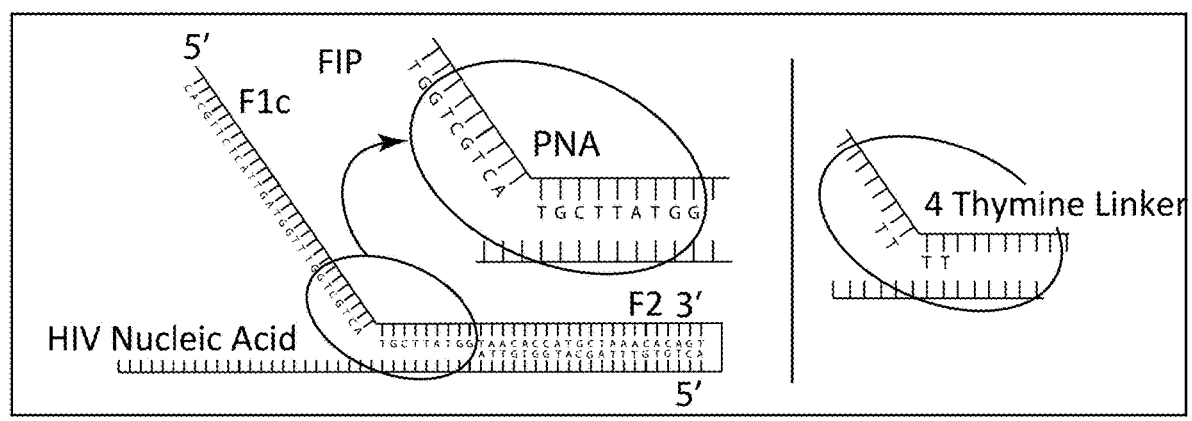
FIG. 8B diagrammatically shows the modified LAMP design.
Figure 9:
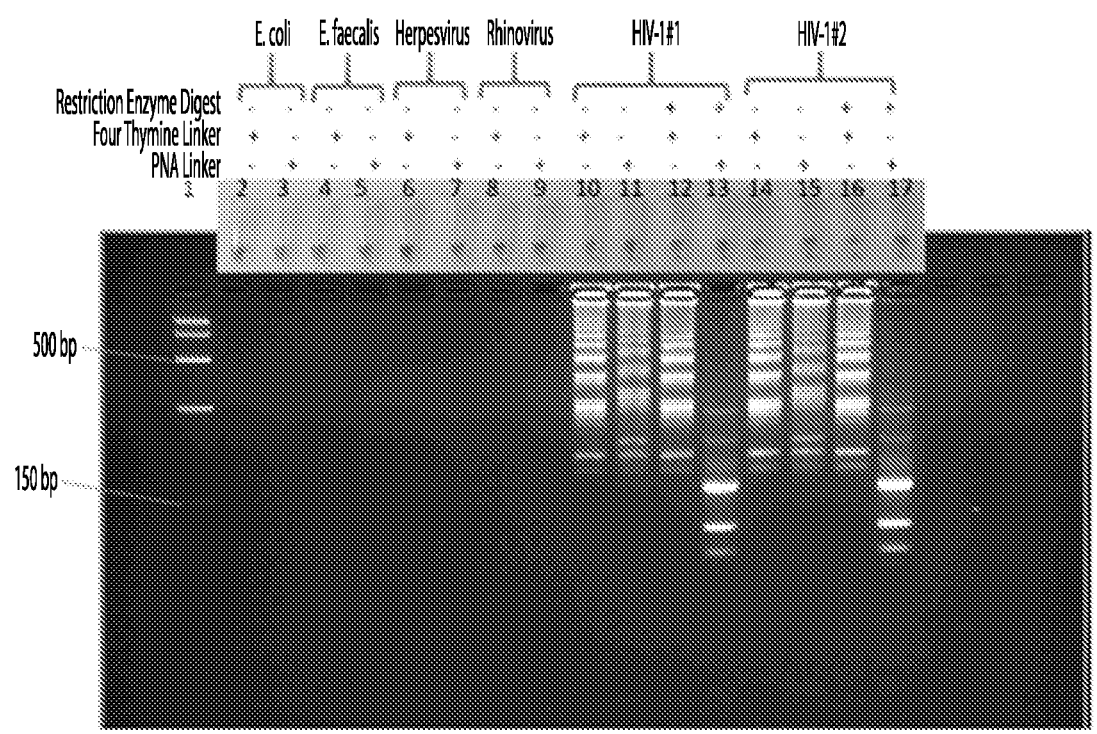
FIG. 9 shows evidence for generation of a PNA linker sequencing using HIV-1 protease gene target.

In addition to the high level of specificity associated with the LAMP assay, the invention introduces an additional degree of specificity. As stated earlier, the LAMP assay uses a minimum of four primers (FIP, BIP, F2, and B2) that recognize six distinct target sequences. Within the FIP (forward inner primer) and BIP (backward inner primer) oligonucleotides, there are two regions consisting of F1c/F2 and B1c/B2 respectively. The invention can replace the four thymine linker with a unique sequence that will co-amplify with the FIP and BIP (FIG. 8B). As a result, the RT-LAMP will generate a unique amplicon that is dependent on the detection of HIV viral RNA and contains a specific sequence complementary to that encoded by the primer linker. The resulting HIV dependent sequence will be the target for detection with a AuNP/PNA probe colorimetric reporter system. The precedence for the generation of a new sequence was recently demonstrated by LAMP based amplification of a five base barcode sequence located within the linker of the FIP primer. The invention demonstrates the feasibility of this approach by modifying an established LAMP assay for the detection of HIV RNA by replacing the TTTT linker with a 16-mer sequence complementary to a PNA probe (FIGS. 8A, 8B and 9).

FIGS. 8A and 8B show the basic principle of LAMP and the modified oligonucleotide design. FIG. 8A is a schematic of the LAMP reaction generating multiple size amplification products. FIG. 8B shows a comparison of traditional LAMP Forward Inner Primer (FIP) with four-thymine linker replaced by the PNA complement sequence as a linker (shown in circles). The same modification is made to the Backward Inner Primer (BIP) (not shown). This design generates the HIV dependent target sequence that serves as the binding site for the complementary PNA probe.

PNAs are synthetic oligonucleotide analogs that contain a neutral backbone as opposed to the negatively charged phosphodiester backbone present in DNA. Due to the change in charge, a PNA-DNA duplex is much more stable than a DNA-DNA duplex. Furthermore, the lack of a 3'-hydroxyl group on the PNA prevents the DNA polymerase from extending the sequence once it is bound to its target. When the PNA binds to its complementary sequence, the melting temperature of the PNA-DNA duplex is much higher than a perfectly matched DNA-DNA duplex. Peptide nucleic acids (PNAs) are commonly used in PCR-clamping applications as blocking agents for wild-type DNA sequences when attempting to identify a mutation in a heterozygous background. If there is a single mismatch in the target DNA, it prevents the PNA from annealing due to a significantly reduced melting temperature compared to a perfectly matched PNA-DNA duplex. Thus the use of a 16-mer PNA provides a level of specificity not attainable using DNA based probes. The uncharged backbone of the PNA makes the PNA/DNA hybridization largely unaffected by salt concentration, ionic strength, and changes in pH. Peptide nucleic acids aggregate gold nanoparticles. When introduced to AuNPs, the PNA changes the aggregative state of the nanoparticles resulting in a visually detectable color change. In solution, un-aggregated AuNPs appear red. When the PNA is added, the AuNPs aggregate and the solution turns blue. In this inventive assay, the PNA will hybridize to the HIV dependent target amplicon leaving the AuNP un-aggregated and appearing red. If the HIV dependent amplicon is not generated the PNA will aggregate the AuNPs resulting in a blue color.

As an alternative to modifying the linker sequence within the FIP/BIP primer sets, the invention also investigate using and may use a PNA specific to a target amplicon generated from traditional poly T FIP/BIP primers. The target of the PNA will be in the RT-LAMP amplicon but not within the primer sequences of the HIV targets. This would eliminate the potential for false positives that could be generated by primer dimerization of the modified FIP/BIP primer sets. In addition, these primer sets are expected to be faster than the modified primer increasing the rate at which the dumbbell structure for LAMP forms.

In the R61 Phase, the approach for Specific Aim #1 is as follows:

To address the development of this assay, this phase preferably adopts the following milestones for specific aim #1. 1) Select target HIV genes and design oligonucleotides, 2) Evaluate multiple stand displacement enzymes for RT-LAMP speed and accuracy, and 3) Evaluate speed and accuracy of RT-LAMP with modified FIP/BIP linker sequences and RT-LAMP using traditional FIP/BIP primers.

This phase would target the p24, protease, integrase and reverse transcriptase genes. Each of these genes has been used for LAMP based detection of HIV. Due to the high mutational rate of the HIV virus, identifying multiple gene targets will reduce the likelihood of a false negative result. An in vivo study determined that the HIV mutation rate is $4.1+/-1.7 \times 10^{-3}$ per base per cell. Targeting of the p24 and protease genes, RT-LAMP was capable of detecting 1,100 copies of viral RNA/tube in heat-treated whole blood and 580 copies of viral RNA in heat treated plasma. Collectively these findings provide evidence that detection of HIV-1 via RT-LAMP is feasible. This phase therefore can investigate a minimum of 10 primers sets per HIV target. For each of the primer sets, this phase would evaluate the incorporation of the linker sequence versus the poly T linker sequence for speed and accuracy. The inventors have found that the poly T linker sequence is faster than the longer PNA linker sequence. Preliminary results comparing time to positive LAMP reactions using conventional and modified FIP/BIP primers by real-time turbidimetry LAMP detection determined the time to positive for poly T FIP/BIP as 29:27 (+/−) 0.07 minutes and time to positive for modified linker FIP/BIP as 35:57 (+/−) 0.07 minutes (data not shown).

Evaluation of time to positive are determined with a pH indicator dye and/or by turbidimetric means. During amplification via polymerase activity, by-products of nucleotide incorporation are magnesium pyrophosphate and hydrogen ions. Turbidity of the reaction increases due to magnesium pyrophosphate accumulation and is detectable using real-time turbidimetry. Hydrogen ions are detected by the pH indicator, phenol red, resulting in a color change from red to yellow. Combinations of strand displacing enzymes with reverse transcriptase effects the rate of the RT-LAMP reaction. To optimize enzyme combinations for the efficient production of the PNA target, we intend to use the New England BioLabs (NEB) WarmStart® LAMP kits. The inventors can determine the rate and efficiency of individual LAMP reactions allowing for controlled evaluations of primer sets and enzyme combinations for generation of our target sequences. Any primer set/enzyme combination that produces a time to positive within 45 minutes can be further evaluated using real-time turbidimetry.

The inventive assay for detection of HIV depends on the generation of a unique amplicon as a result of RT-LAMP. In the presence of HIV RNA, the FIP and BIP primers participate in the amplification of the gene target while simultaneously generating the respective four-thymine linker sequence or the unique sixteen base sequence complimentary to the PNA probe. To test the generation of our unique sequence, the process performed a restriction digest of LAMP amplification products containing the four-thymine sequence or sixteen base PNA probe target. A restriction enzyme was selected that recognizes a sequence internal to the PNA sequence but not found elsewhere in the RT-LAMP amplicon. Restriction enzyme digestion of RT-LAMP amplicons generated using the modified FIP/BIP primers demonstrate generation of the desired PNA probe target sequence (FIG. 6). Only RT-LAMP amplification products containing the PNA sequence digested (lanes 13 and 17) demonstrating the successful incorporation and generation of our PNA target site.

FIG. 9 shows the evidence for generation of the PNA linker sequence using HIV-1 protease gene target. RT-LAMP reaction was performed on negative controls; *E. coli* (lanes 2, 3) *E. faecalis* (lanes 4, 5), Herpesvirus (lanes 6,7) and Rhinovirus (lanes 8,9). Lanes 10-13 and 14-17 are replicate experiments using RNA from an in vitro transcribed HIV-1 plasmid. Compare the change in migration patterns in lanes 10-11 and 14-15 for RT-LAMP products containing the poly T linker (10, 14) versus PNA linker (11, 15). Using the restriction enzyme, Msl1, specific for the PNA linker sequence, only RT-LAMP products containing the PNA sequence were cut eliminating the production of the laddering migrations seen in LAMP reactions. Comparison of lanes 12 with 13 and 16 with 17 demonstrate incorporation of the PNA linker sequence.

Next as to Phase R61, Specific Aim #2 is to optimize a simple visual colorimetric reporter system utilizing AuNP/PNA probe colorimetric detection system that detects the PNA/DNA hybrid from HIV positive RT-LAMP reaction samples.

The inventive assay system comprises a RT-LAMP followed by colorimetric detection using a AuNP/PNA probe. The biochemical characteristics of AuNPs in conjunction with the biochemical characteristics of the PNA lend themselves to this assay. AuNPs have been employed in detection of 1) viral nucleic acid after nucleic acid extraction and Real-Time PCR, 2) detection of a single nucleotide polymorphism in genomic DNA after traditional PCR using ssDNA probes, and 3) determination of protein/DNA dissociation constants. This demonstrates the feasibility of using a AuNP/PNA probe reporter system with RT-LAMP technology.

The use of AuNPs in biological applications is feasible due to the ease of manufacturing, the amenability of spectroscopic analysis of nanoparticles, and the ability to functionalize nanoparticles for use with various spectroscopic techniques. The ability to use AuNPs as a colorimetric reporter is a function of electrostatic interactions of the nanoparticles with single stranded DNA (ssDNA), double stranded DNA (dsDNA), PNA, and buffer components. The HIV RT-LAMP assay will generate single stranded and double stranded DNA molecules with and without higher order secondary structures. Anionic citrate ions coat the AuNPs allowing the repulsive effects of the negatively charged citrate ion to maintain an unaggregated, monodispersed state. The PNA interacts with AuNPs causing them to aggregate. The neutral charge of the PNA and its structural rigidity contribute to the greater affinity of the PNA to its complementary sequence. These properties make the use of AuNP/PNA probe reporter system for the detection of HIV possible.

The approach for Specific Aim #2 is as follows.

This approach adopts the following milestone for specific aim #2, i.e. 1) Determine the optimal combination of AuNP size and PNA length for the most robust color change.

Following generation of the RT-LAMP amplicon, the presence of free PNA or PNA/DNA hybrid will determine the aggregative state of the AuNPs. The presence of free PNA in solution will cause the AuNPs to aggregate resulting in a blue solution (HIV negative), whereas the presence of the PNA/DNA hybrid allows the AuNPs to remain monodispersed resulting in the maintenance of a red solution (HIV positive). Use of nanoparticles from Nanocomposix is believed to eliminate the reproducibility barrier that would exist if one were to perform the citrate-ion coating of the AuNP. The inventors further can evaluate AuNP ranging in size from 5 nm to 100 nm. Evidence indicates that the sensitivity to different PNAs is dependent on nanoparticle size. As a result of these factors, it is possible to further optimize the AuNP/PNA probe reporter system. Optimization will determine the combination of PNA length and diameter of AuNP that results in the most distinct red/blue colors. Optimization will select the most robust color change between blue and red based on the combination of AuNP and PNA for clinical evaluation in specific aim #3.

Work performed in the laboratory using 30 nm AuNPs as a visual colorimetric reporter system demonstrates proof of principle. Three HIV RT-LAMP amplicons were combined with PNA followed by addition of AuNPs. In the reaction containing the RT-LAMP four-thymine linker amplicon, the PNA was free to interact with the AuNPs resulting in a blue solution. Conversely, in the reaction containing the RT-LAMP using the modified linker, formed a DNA/PNA hybrid and did not aggregate the AuNPs allowing the solution to remain red (FIG. 7).

Figure 10:
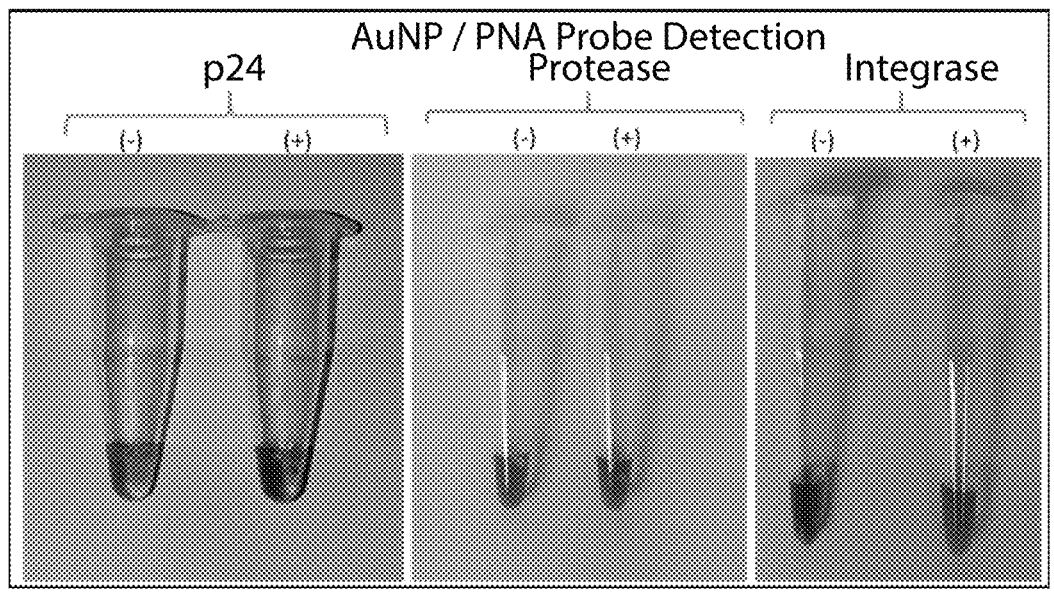
FIG. 10 shows colorimetric AuNP/PNA probe detection differentiating between polyT linker and PNA linker sequences.

FIG. 10 shows that colorimetric AuNP/PNA probe detection differentiates between the polyT linker and PNA linker sequences. Using the RT-LAMP products from three HIV targets, the inventors demonstrated the proof of principle that the AuNP/PNA probe detection system is capable of distinguishing between the polyT linker sequence and the PNA linker sequence. All six of the reactions above were positive for HIV.

Next as to the R61 Phase, Specific Aim #3 is to evaluate and optimize the performance characteristics of the novel assay on clinical samples with known HIV status and viral load levels ranging between 200 and 100,000 copies/ml. Evaluation of the assay includes HIV RNA from positive specimens acquired from Rush University Medical Center Virology Quality Assurance Program and specimens from the State Laboratory of Michigan Department of Health and Human Services (DHHS) in Lansing, Michigan. Evaluation will include assessment of analytical specificity, analytical sensitivity, accuracy, precision, reportable range, limit of detection, interference studies, and reference intervals.

The Approach for Specific Aim #3 is as follows.

This process performs performance characteristic studies on HIV positive/negative specimens. The studies address the analytical specificity, analytical sensitivity, accuracy, precision, reportable range, limit of detection, interference studies, and reference intervals. Within this validation, the inventive development focuses on clinically significant viral load cutoffs of 200, 400, 1000, 10,000 and 100,000 copies/ml. The project will advance to specific aim #4 when: 1) Specific aim #3 meets 95% specificity and 95% sensitivity and 2) the inventive assay compares to the FDA approved Hologic HIV-1 Qualitative HIV-1 Assay where this assay will meet or exceed the parameters set forth by the package insert. For each parameter, results would be no more than 5% different of the results from the package insert.

Upon successful characterization of the RT-LAMP assay followed by AuNP/PNA probe colorimetric detection capable of detection of a minimum of 1000 copies/ml, this process proceeds to specific aim #4.

Next as to the R61 Phase, Specific Aim #4 adapts the TINY system for colorimetric quantification consistent with the AuNP/PNA probe reporter system.

Figures 11A, 11B:
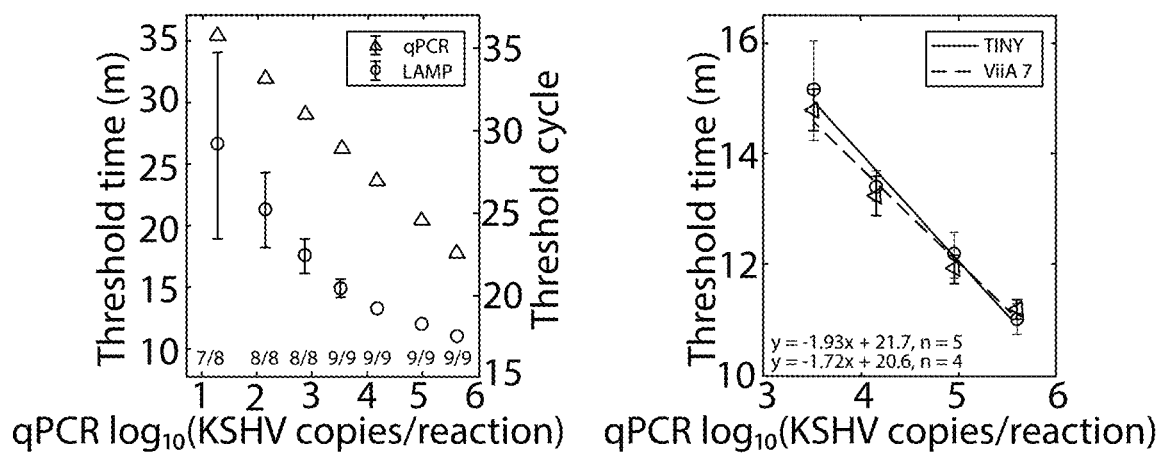

For this application in the detection of HIV, TINY must be capable of performing isothermal amplification followed by colorimetric detection of PNA/DNA hybrids. TINY has been used in a similar application for quantitative nucleic acid detection of Kaposi's sarcoma from skin biopsy samples from patients. To quantify KSHV load in unknown-concentration skin biopsy samples, standard curves with known copy numbers of the KS target gene, ORF 26, were generated from recombinant plasmid DNA, and DNA extracted from a KSHV+ cell line, BC-3. Amplification data from the plasmid or cell line standards was compared against that obtained from the unknown biopsy samples to approximate KSHV content. The following observations are drawn from the KSHV+ cell line (BC-3) standards, as the DNA in these samples was extracted using the same procedure as for the human biopsy samples (DNeasy, Qiagen). The qPCR assay (the gold-standard) proved quantitative for all concentrations of standards (FIG. 11A). The LAMP assay produced repeatable threshold times for the four highest standards tested ($3.2 \times 10^3$ to $3.9 \times 10^5$ copies/reaction), but at lower concentrations threshold time no longer linearly predicted starting DNA concentration. At the lowest concentration tested (19 KSHV copies/reaction), the LAMP assay amplified in 7 of 8 trials, and at the second lowest concentration (135 copies/reaction), the LAMP assay amplified in 8 of 8 trials. Testing amplified calibration standard samples using LAMP in both TINY and a commercial qPCR machine (ViiA 7 from Thermo Fisher Scientific, set to a constant 68° C.). Similar threshold times were observed for both machines (FIG. 11B), confirming that TINY can perform quantitative, isothermal assays with results that are equivalent to those from commercial systems.

Standard samples are amplified using LAMP in both TINY and a commercial qPCR machine (ViiA 7 from Thermo Fisher Scientific, set to a constant 68° C.). Similar threshold times were observed for both machines (FIGS. 11A and 11B), confirming that TINY can perform quantitative, isothermal assays with results that are equivalent to those from commercial systems.

Figure 12:
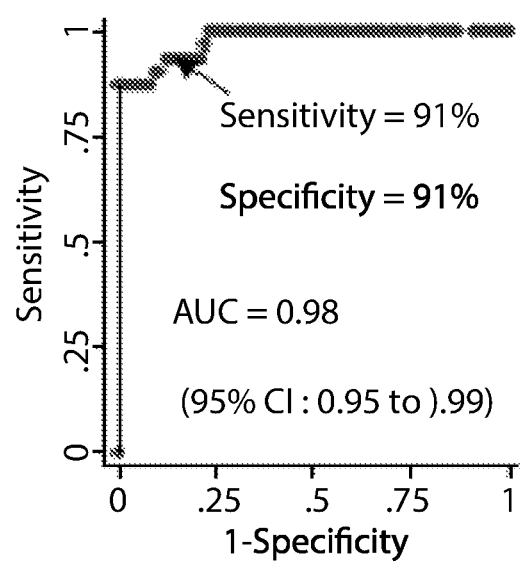
FIG. 12 graphically shows an ROC curve depicting performance of the LAMP for diagnosis of KS compared to US-based pathologic gold standard.

FIGS. 11A and 11B 8 shows the TINY performance results. FIG. 11A shows amplification results for the BC-3 cell line standards, as tested by qPCR and LAMP (LAMP results include trials from both TINY and the ViiA 7). At the bottom is shown the number of samples which amplified using the LAMP assay at a particular concentration, divided by the number of total trials performed. Each sample was run in duplicate using the qPCR assay. Error bars: standard deviation. FIG. 11B shows standard curves as measured by TINY and the ViiA 7 commercial machine, both performing the LAMP assay using BC-3 cell line standards. Error bars: SD To assess how TINY performs under optimal conditions with experienced operators, we have examined 128 Ugandan biopsy specimens using TINY performed under controlled conditions. Using U.S. pathology-derived "KS Present" and "KS Absent" as the true positive and true negative reference groups, we interrogated various cutpoints of TINY for their sensitivity and specificity for KS diagnosis using an ROC curve (FIG. 12). The AUC for TINY was 0.98 (95% confidence interval: 0.95 to 0.99). At the optimal cutpoint that balances sensitivity and specificity (fluorescent signal at 17 minutes), sensitivity was 91% and specificity was 91%. This substantiates the hypothesis that quantitation of KSHV DNA content, as performed by a portable device under optimal conditions in a controlled laboratory setting, can diagnose KS with high sensitivity and specificity.

The approach for Specific Aim #4 is as follows.

In this aim, the process adapts the device to be compatible with the novel reporter system developed here and implement a novel sample processing technique to enable blood processing. The first stage of this makes mechanical modifications to the TINY to adapt the optical system to enable analysis of the colorimetric signal rather than the florescence signal used in the current approach. This is relatively straightforward involving mostly electrical modifications to the system to replace the current LED and optical modifications to replace the current filters. Once completed a series of experiments ensures proper quantification of the samples using the AuNP reporter scheme, which is done across the range of expected clinical concentrations. When complete, validation is done using the same samples and metrics for success specific Aim 3 to ensure that that the same performance is obtained with the TINY system as with the gold standard methods.

For the next R33 Phase, Specific Aim #5 is as follows, wherein Specific Aim #5 comprises clinical validation of the TINY system for HIV detection.

The approach for Specific Aim #5 includes performance characteristic studies in a clinical setting using the same HIV positive/negative specimens from specific aim #3. The studies address the analytical specificity, analytical sensitivity, and accuracy, precision, reportable range, limit of detection, interference studies, and reference intervals. Within this validation, the focus is on clinically significant viral load cutoffs of 200, 400, 1000, 10,000 and 100,000 copies/ml.

For the R33 Phase, Specific Aim #6 involves the validation of the TINY system for HIV detection in an austere environment.

The approach for Specific Aim #6 involves performance of performance characteristic studies in an austere setting using HIV positive/negative specimens. The studies address the analytical specificity, analytical sensitivity, and accuracy, precision, reportable range, limit of detection, interference studies, and reference intervals. Within this validation, the focus is on clinically significant viral load cutoffs of 200, 400, 1000, 10,000 and 100,000 copies/ml.

In this manner, the inventive assay is validated and optimized.

Although particular preferred embodiments of the invention have been disclosed in detail for illustrative purposes, it will be recognized that variations or modifications of the disclosed apparatus, including the rearrangement of parts, lie within the scope of the present invention.

What is claimed:

1. A method of rapidly performing a diagnostic assay for detection of nucleic acids (DNA/RNA), comprising:
    performing a LAMP reaction with a Loop Mediated Isothermal Amplification (LAMP) device to process a test solution and detect at least one specific nucleic acid sequence in said test solution that defines a target dependent sequence of a nucleic acid that is targeted for detection by said rapid diagnostic assay, wherein said LAMP reaction performs isothermal amplification of said target dependent sequence of the nucleic acid, said LAMP reaction using a plurality of primers to detect target sequences wherein one or more of said primers have a poly T linker replaced with a peptide nucleic acid (PNA) sequence to form a PNA/DNA hybrid that corresponds to and binds with said target dependent sequence of said nucleic acids; and
    providing a colorimetric reporter system using gold nanoparticles (AuNP) aggregatable with a peptide nucleic acid (PNA); and
    using said colorimetric reporter system to identify and detect said target dependent sequence of said nucleic acid sequences and identify the presence of said target dependent sequence.

2. The method according to claim 1, wherein detection of said presence of said target dependent sequence indicates the presence of a pathogen associated therewith.

3. The method according to claim 1, wherein using s a minimum of four said primers identified as FIP, BIP, F3, B3 in said LAMP reaction, which are used to detect a plurality of said target sequences.

4. The method according to claim 3, including the step of modifying at least one of said FIP and BIP primers to have said poly T linker replaced with said PNA sequence corresponding with said target dependent sequence of nucleic acids.

5. The method according to claim 4, including the step of generating with said LAMP a specific DNA sequence that is the complement of, and target for, said PNA to form said PNA/DNA hybrid.

6. The method according to claim 5, including the step of detecting a presence of said PNA/DNA hybrid using said colorimetric reporter system, wherein aggregative properties of said gold nanoparticles (AuNPs) with said PNAs allow use of said AuNPs to detect said PNA/DNA hybrids.

7. The method according to claim 6, including the step of visually indicating the presence or absence of said target dependent sequence of said nucleic acid sequences wherein said AuNPs when non-aggregated appearing red in solution while said AuNPs when aggregated appear blue in solution.

8. The method according to claim 1, wherein said LAMP reaction is a Reverse Transcriptase-LAMP reaction.

9. The method according to claim 1, wherein said target dependent sequence of nucleic acids correspond to and indicate the presence of a target pathogen.

10. The method according to claim 1, wherein said target dependent sequence corresponds to a target pathogen being tested for, and said target pathogen is one of a virus or bacteria.

* * * * *